United States Patent [19]
Rodgers et al.

[11] Patent Number: 5,639,468
[45] Date of Patent: Jun. 17, 1997

[54] METHOD FOR REDUCING OR PREVENTING POST-SURGICAL ADHESION FORMATION USING MANOALIDE AND ANALOGS THEREOF

[75] Inventors: Kathleen Elizabeth Rodgers, Long Beach; Gere Stodder diZerega, Pasadena, both of Calif.

[73] Assignee: University of Southern California, Los Angeles, Calif.

[21] Appl. No.: 479,678

[22] Filed: Jun. 7, 1995

[51] Int. Cl.$^6$ .............................. A61K 9/127; A61K 9/50
[52] U.S. Cl. .................... 424/426; 424/423; 424/443; 424/450; 424/489; 424/424; 514/772.3; 514/777; 514/778; 514/781; 514/945
[58] Field of Search .................... 424/426, 450, 424/489, 424, 423, 428, 443; 514/772.3, 778, 781

[56] References Cited

U.S. PATENT DOCUMENTS

| | | | |
|---|---|---|---|
| 4,447,445 | 5/1984 | Jacobs et al. | 424/279 |
| 4,616,089 | 10/1986 | Jacobs et al. | 549/323 |
| 4,786,651 | 11/1988 | Wheeler | 514/460 |
| 4,789,749 | 12/1988 | Jacobs et al. | 549/313 |
| 4,839,385 | 6/1989 | Maullem et al. | 514/473 |
| 4,935,530 | 6/1990 | Lee | 549/214 |
| 4,937,254 | 6/1990 | Sheffield et al. | 514/420 |
| 4,952,605 | 8/1990 | Jacobs et al. | 514/473 |
| 5,037,811 | 8/1991 | Lee | 514/99 |
| 5,045,564 | 9/1991 | Lee | 514/471 |
| 5,169,963 | 12/1992 | Lee | 549/222 |
| 5,171,864 | 12/1992 | Lee | 549/222 |
| 5,183,906 | 2/1993 | Lee et al. | 549/218 |
| 5,290,777 | 3/1994 | McConnell et al. | 514/254 |
| 5,322,953 | 6/1994 | Lee et al. | 549/214 |

FOREIGN PATENT DOCUMENTS

| | | |
|---|---|---|
| 71041/87 | 6/1988 | Australia . |
| 0372941A2 | 6/1990 | European Pat. Off. . |
| WO91/16055 | 10/1991 | WIPO . |

OTHER PUBLICATIONS diZerega, G.S. & Rodgers, K.E. (1992), "Prevention of Postoperative Adhesions," in *The Peritoneum*, diZerega, G. S. & Rodgers, K.E., eds., Springer-Verlag, New York, pp. 307–369.

Elkins, T.E., (1990), "Can a Pro–Coagulant Substance Prevent Adhesions?" in *Treatment of Post–Surgical Adhesions*, diZerega, G.S. et al., eds., Wiley–Liss, New York, pp. 103–112.

Rodgers, K.E. (1990), "Nonsteroidal anti–inflammatory drugs (NSAIDs) in the treatment of Postsurgical adhesion," in *Treatment of Post–Surgical Adhesions*, diZerega, G.S. et al., eds., Wiley–Liss, New York, pp. 119–129.

Bennett et al. (1987), "Differential–effects of manoalide on secreted and intracellular phospholipases," *Biochem. Pharm.*, vol. 36(5), pp. 733–740.

Glaser et al. (1987), "Inactivation of bee venom phospholipase $A_2$ by manoalide. A model based on the reactivity of manoalide with amino acids and peptide sequences," *Biochem. Pharm.*, vol. 36(13), pp. 2079–2086.

Jacobson et al. (1990), "Inactivation of human synovial fluid phospholipase $A_2$ by the marine natural product, manoalide," *Biochem., Pharm.*, vol. 39, pp. 1557–1564.

Mayer et al. (1988), "Regulation of eicosanoid biosynthesis in vitro and in vivo by the marine natural product manoalide: A potent inactivator of venom phospholipases," *J. Pharm. and Exp. Therapeutics*, vol. 244(3), pp. 871–878.

Bennett et al. (1987), "Inhibition of phosphoinositide–specific phospholipase C by manoalide," *Molecular Pharm.*, vol. 32, pp. 587–593.

Mayer et al. (1993), "Modulation of superoxide anion generation by manoalide, arachidonic acid and staurosporine in liver infiltrated neutrophils in a rat model of endotoxemia," *J. Pharm. and Exp. Therapeutics*, vol. 267, pp. 400–409.

Mayer et al. (1994), "Modulation of superoxide generation in vivo lipopolysaccharide–primed kupffer cells by staurosporine, okadaic acid, manoalide, arachidonic aid, genistein and sodium orthovanadate," *J. Pharm. and Exp. Therapeutics*, vol. 268, pp. 238–247.

Locati et al. (1994), "Rapid induction of arachidonic acid release by monocyte chemotactic protein–1 and related chemokines. Role of $Ca^{2+}$ influx, synergism with platelet–activating factor and significance for chemotaxis," *J. Biological Chemistry*, vol. 269, pp. 4746–4753.

Lennartz et al. (1991), "Arachidonic acid is essential for IgG Fc receptor–mediated phagocytosis by human monocytes," *J. Immunology*, vol. 147, pp. 621–626.

Lefkowith et al. (1992), "Phospholipase activation during monocyte adherence and spreading," *J. Immunology*, vol. 149, pp. 1729–1735.

(List continued on next page.)

*Primary Examiner*—Thurman K. Page
*Assistant Examiner*—James M. Spear
*Attorney, Agent, or Firm*—McDonnell Boehnen Hulbert & Berghoff

[57] ABSTRACT

Compositions and methods for minimizing or preventing post-surgical adhesion formation between tissue, e.g., organ, surfaces in body cavities, whereby an effective therapeutic amount of manoalide or analog thereof is administered to the target injury site for a period of time sufficient to permit tissue repair. Manoalide or analog thereof is preferably administered in conjunction with a delivery vehicle (e.g., microcapsules, microspheres, biodegradable polymer films, lipid-based delivery systems such as liposomes and lipid foams, crystalloid and viscous instillates and absorbable mechanical barriers) useful for maintaining local concentrations of the inhibitor at the injury site at an effective level for a sustained period of time.

21 Claims, No Drawings

OTHER PUBLICATIONS

Zhang and Dennis (1988), "Purification and characterization of a lysophospholipase from a macrophage–like cell line P388D1," *J. Biological Chemistry*, vol. 263(20), pp. 9965–9972.

Deems et al. (1987), "The inhibition of phospholipase $A_2$ by manoalide and manoalide analogues," *Biochimica et Biophysica Acta*, vol. 917, pp. 258–268.

deVries et al. (1991), "AGN 190383, a novel phospholipase inhibitor with topical anti–inflammatory activity," *Agents and Actions*, vol. 34(1/2), pp. 70–72.

Reynolds et al. (1991), "Inhibition of venom phospholipase A2 by Manoalide and Manoalogue. Stoichiometry of incorporation," *J. Biological Chemistry*, vol. 266, pp. 16512–16517.

Snyder et al. (1992), "Evidence that phospholipase $A_2$ ($PLA_2$) inhibitors can selectively block $PLA_2$–mediated contractions of guinea pig lung pleural strips," *J. Pharm. and Exp. Therapeutics*, vol. 262, pp. 1147–1153.

Glaser et al. (1989), "Manoalide: Structure activity studies and definition of the pharmacophore for phospholipase $A_2$ inactivation," *Molecular Pharmacology*, vol. 36, pp. 782–788.

Kobayahi et al. (1993), "Luffariolides F and G, new manoalide derivatives from the okinawan marine sponge *Luffarielle sp.*," *J. Natural Products*, vol. 56, pp. 436–439.

Konig et al. (1992), "Four new antibacterial sesterterpenes from a marine sponge of the genus *Luffariella*, *J. Natural Products*," vol. 55, pp. 174–178.

Ortiz et al. (1993), "Molecular model of the interaction of bee venom phospholipase $A_2$ with manoalide," *J. Medicinal Chemistry*, vol. 36, pp. 1866–1879.

Lewis, D.H. (1990), "Controlled Release of Bioactive Agents from Lactide/Glycolide Polymers," in *Biodegradable Polymers as Drug Delivery Systems*, Jason & Langer, eds., pp. 1–41.

Hockel, M. et al. (1987), "Prevention of Peritoneal Adhesions in the Rat with Sustained Intraperitoneal Dexamethasone Delivered by a Novel Therapeutic System," *Annales Chirurgiae et Gynaecologiae*, vol. 76, pp. 306–313.

Rodgers, K. et al. (1990), "Intraperitoneal Tolmetin Prevents Postsurgical Adhesion Formation in Rabbits," *Int. J. Fertil.*, vol. 35, pp. 40–45.

Kim, T. et al. (1993) "Extended–release formulation of morphine for subcutaneous administration," *Cancer Chemother. Pharmacol.*, vol. 33, pp. 187–190.

Chatelut, E. et al. (1993) "A slow–release methotrexate formulation for intrathecal chemotherapy," *Cancer Chemother. Pharmacol.*, vol. 32, pp. 179–182.

Takino et al. (1994) "Long Circulating Emulsion Carrier Systems for Highly Lipophilic Drugs," *Biol. Pharm. Bull.*, vol. 17, pp. 121–125.

Abe, H. et al.(1990), "The Effect of intra–peritoneal Administration of Sodium Tolmetin–Hyaluronic Acid on the Postsurgical Cell Infiltration in vivo," *J. Surg. Res.*, vol. 49, pp. 322–327.

Johnson and Johnson Medical, Inc., New Brunswick, New Jersey INTERCEED(TC7) Adhesion Barrier Study Group, (1989), "Prevention of postsurgical adhesions by INTERCEED(TC7), an absorbable adhesion barrier: a prospective, randomized multicenter clinical study," *Fertility and Sterility*, vol. 51, pp. 933–938.

Diamond, M. P. et al. (1991), "Synergistic effects of INTERCEED(TC7) and heparin in reducing adhesion formation in the rabbit uterine horn model," *Fertility and Sterility*, vol. 55, pp. 389–394.

Diamond, M.P. et al. (1991), "Adhesion reformation: reduction by the use of INTERCEED(TC7) plus heparin," *J. Gyn. Surg.*, vol. 7, pp. 1–6.

Nishimura, K. et al. (1984), "The Use of Ibuprofen for the Prevention of Postoperative Adhesions in Rabbits," *Am. J. Med.*, vol. 77, pp. 102–106.

Derwent Search Results dated May 24, 1995.

METHOD FOR REDUCING OR PREVENTING POST-SURGICAL ADHESION FORMATION USING MANOALIDE AND ANALOGS THEREOF

FIELD OF THE INVENTION

The present invention relates to manoalide and analogs thereof and their use thereof in a method for reducing or preventing post-operative adhesion formation between tissue, e.g., organ, surfaces in a body cavity.

BACKGROUND OF THE INVENTION

Adhesion formation, in particular following peritoneal surgery, is a major source of postoperative morbidity and mortality. Appendectomy and gynecologic surgery are the most frequent surgical procedures implicated in clinically significant adhesion formation. The most serious complication of intraperitoneal adhesions is intestinal obstruction; in addition, adhesions are associated with chronic or recurrent pelvic pain and infertility in females.

The pathogenesis of adhesion formation is complex and not entirely understood. The first step is believed to involve excess fibrin deposition to form a scaffold. Organization of the fibrin scaffold by cellular elements, including fibroblasts and mesothelial cells, then follows.

Various approaches for the prevention of adhesion formation have been actively explored [diZerega, G. S. & Rodgers, K. E., "Prevention of Postoperative Adhesions," in "The Peritoneum," diZerega, G. S. & Rodgers, K. E., eds., Springer-Verlag, New York, pp. 307–369 (1992)]. In general, the treatments fall into three categories: prevention of fibrin deposition in the peritoneal exudate, reduction of local tissue inflammation; and removal of fibrin deposits.

Therapeutic attempts to prevent fibrin deposition include peritoneal lavages to dilute or wash away fibrinous exudate, surgical techniques to minimize tissue ischemia and introduction of barriers to limit apposition of healing serosal surfaces. Although the use of agents affecting coagulation of the fibrinous fluid has also been proposed, results obtained to date suggest that the use of procoagulants in areas of substantial bleeding may actually promote adhesion formation [Elkins, T. E., "Can a Pro-Coagulant Substance Prevent Adhesions?" in "Treatment of Post-Surgical Adhesions," diZerega, G. S. et al., eds., Wiley-Liss, New York, pp. 103–112 (1990)].

Physical barriers have been used in attempts to prevent adhesion formation by limiting tissue apposition during the critical period of peritoneal healing, thereby minimizing the development of fibrin matrix between tissue surfaces. Barrier agents which have been employed include both mechanical barriers and viscous solutions. Mixed results have been obtained using a barrier comprising a thin sheet of expanded poly-tetrafluoroethylene; in any event, such a membrane is less than ideal, as it must be sutured into place and is nonabsorbable. While an absorbable barrier (for example, a barrier made of oxidized regenerated cellulose) would be preferable, not all studies have demonstrated the efficacy of such barriers in preventing adhesions. Liquid barriers have also been considered for use in preventing adhesions; for example, chondroitin sulfate and carboxymethyl cellulose have both shown some promise in animal models. In addition, solution of dextran 70 (molecular weight=70,000) has been the subject of a number of clinical studies. Not all clinical evaluations of 32% dextran 70 have found a therapeutic effect, however, and the clinical use of the solution is also associated with clinically important side effects.

Anti-inflammatory drugs have been evaluated for their effects on postoperative adhesion formation, as they may limit the release of fibrinous exudate in response to inflammation at the surgical site. Two general classes of these drugs were tested: cortico-steroids and nonsteroidal anti-inflammatory drugs. The results of corticosteroid use in animal studies have generally not been encouraging, and clinical use of corticosteroids is limited by their other pharmacologic properties. While experimental evaluations of nonsteroidal anti-inflammatory drugs in postoperative adhesion formation show promise [Rodgers, K. E., "Nonsteroidal anti-inflammatory drugs (NSAIDs) in the treatment of Postsurgical adhesion," in "Treatment of Post-Surgical Adhesions," diZerega, G. S. et al., eds., Wiley-Liss, New York, pp. 119–129 (1990)], clinical evaluations of these drugs for adhesion prevention is needed.

The third approach explored to date involves the removal of fibrin deposits. Although proteolytic enzymes (e.g., pepsin, trypsin and papain) should theoretically augment the local fibrinolytic system and limit adhesion formation, these enzymes are rapidly neutralized by peritoneal exudates rendering them virtually useless for adhesion prophylaxis. While various fibrinolytics (for example, fibrinolysin, streptokinase and urokinase) have been advocated, a potential complication to the clinical use of these enzymes in postoperative therapy is excessive bleeding resulting from their administration. Topical application of a recombinant tissue plasminogen activator (rt-PA) has been shown to reduce adhesion formation in a variety of animal models; further research is necessary to develop suitable delivery systems to provide this drug to the surgical site and identify the postoperative time when adhesion prevention is feasible.

To date, no single therapeutic approach has proven universally effective in preventing formation of postoperative intraperitoneal adhesions. Therefore, there is a need for compositions and methods which may be used safely and effectively to prevent adhesion formation in a variety of different contexts.

OBJECTS OF THE INVENTION

It is an object of the present invention to provide manoalide or analogs thereof for use in preventing or minimizing adhesion formation.

It is another object of the invention to provide a method for reducing or preventing post-surgical adhesion formation between tissue surfaces in body cavities which employ manoalide or analogs thereof.

These and other objects of the invention will be apparent in light of the detailed description below.

SUMMARY OF THE INVENTION

The present invention relates to manoalide and manoalide analogs (which include manoalide derivatives) thereof and their use in a method for reducing or preventing adhesion formation between tissue, e.g., organ, surfaces in body cavities comprising administering to a subject an effective amount of at least one manoalide or analog thereof. Manoalide or analogs thereof are preferably administered in conjunction with a drug delivery system which maintains an effective concentration of the compound at a site of potential adhesion formation during the perioperative interval.

DETAILED DESCRIPTION OF THE INVENTION

All literature references, patents and patent applications cited in this application are incorporated herein in their entirety.

The inventive composition and method are useful in minimizing or preventing formation of adhesions between organ surfaces (not cell-to-cell adhesion), the most common cause of which is prior surgery. The inventive composition and method have been shown to be especially effective in preventing adhesion formation in the peritoneum following surgery. In addition, the present invention finds utility in other contexts, e.g., for cardiovascular, orthopedic, thoracic, ophthalmic, CNS and other uses, where prevention of the formation of adhesions is a significant concern. For example, prevention of adhesion formation or drug loculation during the intraperitoneal administration of chemotherapeutic agent is contemplated as within the scope of the present invention. For the purposes of the following discussion, attention is directed primarily to description of compositions and methods useful in inhibiting peritoneal adhesion formation.

The present invention is based on the discovery that manoalide, an anti-inflammatory compound isolated from marine sponges, as structurally defined in U.S. Pat. No. 5,322,953, is useful in reducing or preventing the formation of adhesions between tissue surfaces in body cavities following surgical procedures. Manoalide's anti-inflammatory properties are thought to be the result of irreversible inhibition of phospholipase $A_2$ (PLA), a major enzyme involved in the metabolism of phospholipids into bioactive substances such as platelet activating factor (PAF) and arachidonate metabolites, e.g. prostaglandins, thromboxanes and leukotrienes. These metabolites have been implicated in various pathological conditions. Bennett et al (1986) "Differential Effects of manoalide on secreted and intracellular phospholipases," Biochem. Pharm., Vol. 36, pp. 733–740. Prior to the present invention, however, the use of manoalide or analogs thereof in preventing post-surgical adhesions was unknown.

While the present invention is not bound to any particular theory of operation, it is believed that manoalide or analogs thereof may inhibit adhesion formation through a variety of mechanisms. For example, manoalide inhibits the production of various lipid mediators of inflammation, including prostaglandin $E_2$, through inhibition of PLA. Glaser et al. (1987), "Inactivation of bee venom phospholipase $A_2$ by manoalide. A model based on the reactivity of manoalide with amino acids and peptide sequences," Biochem. Pharm. Vol. 36(13), pp. 2079–2086; Jacobson et al. (1990), "Inactivation of human synovial fluid phospholipase $A_2$ by the marine natural product, manoalide," Biochem. Pharm., Vol. 39, pp. 1557–1564. Mayer et al. (1988), "Regulation of eicosanoid biosynthesis in vitro and in vivo by the marine natural product manoalide: A potent inactivator of venom phospholipases," J. Pharm. and Exp. Therapeutics, Vol. 244(3), pp. 871–878.

Manoalide inhibits production of leukotriene $C_4$, but this action is variable depending upon the stimulus used. Mayer et al. (1988), "Regulation of eicosanoid biosynthesis in vitro and in vivo by the marine natural product manoalide: A potent inactivator of venom phospholipases," J. Pharm. and Exp. Therapeutics, Vol. 244(3), pp. 871–878.

Manoalide also inhibits the activity of the enzyme, phospholipase C, which is involved in signal transduction. Bennett et al. (1987), "Inhibition of phosphoinositide-specific phospholipase C by manoalide," Molecular Pharm., Vol. 32, pp. 587–593.

As is well recognized in the art, however, no one of these possible mechanisms of action of manoalide or analogues would in and of itself be sufficient to enable one to predict whether these compounds would have any utility in reduction of adhesion formation. Indeed, several properties of manoalide would suggest that this compound would be ineffective at reducing adhesion formation. In addition, not all forms of PLA are inhibited by manoalide. Bennett et al. (1987), "Differential-effects of manoalide on secreted and intracellular phospholipases," Biochem. Pharm., Vol. 36(5), pp. 733–740.

For example, manoalide inhibits various macrophage functions which are thought to be important in the resolution of fibrin deposition, clearance of debris and orchestration of healing that are important in adhesion-free peritoneal healing. Such functions, which are inhibited by manoalide, were previously shown to be elevated after in vivo exposure to tolmetin postoperatively (a compound previously shown to reduce adhesion formation). Rodgers, K. E., "Nonsteroidal anti-inflammatory drugs (NSAIDs) in the treatment of Post-surgical adhesion," in "Treatment of Post-Surgical Adhesions," diZerega, G. S. et al., eds., Wiley-Liss, New York, pp. 119–129 (1990). For instance, manoalide inhibits the production on superoxide anion. Mayer et al. (1993), "Modulation of superoxide anion generation by manoalide, arachidonic acid and staurosporine in liver infiltrated neutrophils in a rat model of endotoxemia," J. Pharm. and Exp. Therapeutics, Vol. 267, pp. 400–409; Mayer et al. (1994), "Modulation of superoxide generation in vivo lipopolysaccharide-primed kupffer cells by staurosporine, okadaic acid, manoalide, arachidonic aid, genistein and sodium orthovanadate," J. Pharm. and Exp. Therapeutics, Vol. 268, pp. 238–247. Manoalide blocks also monocyte chemotaxis and phagocytosis. Locati et al. (1994), "Rapid induction of arachidonic acid release by monocyte chemotactic protein-1 and related chemokines. Role of $Ca^{2+}$ influx, synergism with platelet-activating factor and significance for chemotaxis," J. Biological Chemistry, Vol. 269, pp. 4746–4753. Lennartz et al. (1991), "Arachidonic acid is essential for IgG Fc receptor-mediated phagocytosis by human monocytes," J. Immunology, Vol. 147, pp. 621–626. Finally, manoalide impairs monocyte adherence and spreading. Lefkowith et al. (1992), "Phospholipase activation during monocyte adherence and spreading," J. Immunology, Vol. 149, pp. 1729–1735.

Accordingly, in light of these possible mechanisms of action of manoalide or analogs thereof, there is no suggestion that such compounds would in and of themselves have any utility in preventing or reducing post-surgical adhesion formation.

Manoalide has been shown in the Examples below to be a useful compound for reducing or preventing post-surgical adhesion formation. It will be understood that analogs and derivatives of manoalide which are also capable of inhibiting PLA activity are also contemplated for use in the present invention. Suitable, but non-limiting examples, of manoalide analogs and derivatives are described for instance in Zhang and Dennis (1988), "Purification and characterization of a lysophospholipase from a macrophage-like cell line P388D1," J. Biological Chemistry, Vol. 263(20), pp. 9965–9972; Deems et al. (1987), "The inhibition of phospholipase $A_2$ by manoalide and manoalide analogues," Biochimica et Biophysica Acta, Vol. 917, pp. 258–268; deVries et al. (1991), "AGN 190383, a novel phospholipase inhibitor with topical anti-inflammatory activity," Agents and Actions, Vol. 34(½), pp. 70–72; Reynolds et al. (1991), "Inhibition of venom phospholipase A2 by Manoalide and Manoalogue. Stoichiometry of incorporation," J. Biological Chemistry, Vol. 266, pp. 16512–16517; Snyder et al. (1992), "Evidence that phospholipase $A_2$ ($PLA_2$) inhibitors can selectively block PLA$_2$-mediated contractions of guinea pig lung pleural strips," *J. Pharm. and Exp. Therapeutics*, Vol. 262, pp. 1147–1153; Glaser et al. (1989), "Manoalide: Structure activity studies and definition of the pharmacophore for phospholipase A$_2$ inactivation," *Molecular Pharmacology*, Vol. 36, pp. 782–788; Kobayashi et al. (1993), "Luffariolides F and G, new manoalide derivatives from the okinawan marine sponge *Luffariella sp.*," *J. Natural Products*, Vol. 56, pp. 436–439; Konig and Sticher (1992), "Four new antibacterial sesterterpenes from a marine sponge of the genus Luffariella", *J. Natural Products*, Vol. 55, pp. 174–178; Ortiz et al. (1993), "Molecular model of the interaction of bee venom phospholipase A$_2$ with manoalide," *J. Medicinal Chemistry*, Vol. 36, pp. 1866–1879. Other representative manoalide analogs and derivatives contemplated for use in the present invention are described in U.S. Pat. Nos. 4,952,605; 4,616,089; 4,789,749; 4,839,385; 4,786,651; 4,447,445; 5,322,953; 5,290,777; 5,171,864; 5,169,963; 5,183,906; 5,037,811; 5,045,564; 4,935,530; and in AU 8771041; WO 91/16055; EP 372941.

In practicing this invention, the preferred manoalide analogs and derivatives are those which have little or no toxicity at the local and systemic level and are suitable for topical use in animals, including humans. Methods which may be employed in screening and identifying useful manoalide analogs and derivatives are disclosed, for example, in U.S. Pat. No. 5,322,953, which is incorporated herein by reference in its entirety.

Pursuant to the method of the present invention, manoalide or analogs thereof is maintained at an effective concentration at the site of potential adhesion formation for a period of time sufficient to permit substantial re-epithelialization. Manoalide or analogs thereof is typically administered over the perioperative interval, which for purposes of the present invention may include time shortly prior to surgery through the surgery itself up to some time after completion of surgery.

The effective therapeutic concentrations of manoalide or analogs thereof are ones that minimizes or prevents post-surgical adhesion formation between tissues surfaces in body cavities. Typically, the concentrations of manoalide or analogs thereof which can be administered would be limited by efficacy at the lower end and the solubility or toxicity of the compound at the upper end. The general and preferred concentrations for use in the invention are as follows:

| General Range | Preferred Range |
| --- | --- |
| 0.001 ng–1 mg/hr | 0.1 ng–0.01 mg/hr |
| 0.0004 ng–0.4 mg/hr/kg | 0.04 ng–0.004 mg/hr/kg |
| 0.000067 ng–0.067 mg/hr/cm$^2$ | 0.0067 ng–0.67 µg/hr/cm$^2$ |
| 0.000027 ng–0.0267 mg/hr/cm$^2$/kg | 0.0027 ng–0.00027 mg/hr/cm$^2$/kg |

As defined herein, kg refers to body weight of the subject and cm$^2$ refers to the surface area of the site to be treated. The wt/hr/cm$^2$ ranges are generally used for administration of manoalide with liquid or barrier delivery systems.

Manoalide may be administered directly following the surgical procedure in a suitable vehicle, for example, a solution of 5% DMSO or 10% ethanol in saline, to a site at which it is desired to reduce or prevent adhesion formation. Pursuant to preferred embodiments of the present invention, however, manoalide is administered in a single dose delivery (for example, prior to skin closure after surgery) using a drug-delivery system which enables the maintenance of requisite concentrations of the compound for a period of time sufficient for re-epithelialization. A suitable drug-delivery system would itself be essentially non-inflammatory and nonimmunogenic and would permit release of manoalide so as to maintain effective levels thereof over the desired time period.

A large variety of alternatives are known in the art as suitable for purposes of sustained release and are contemplated as within the scope of the present invention. Suitable delivery vehicles include, but are not limited to, the following: microcapsules or microspheres; liposomes and other lipid-based release systems; crystalloid and viscous instillares; absorbable and/or biodegradable mechanical barriers; and polymeric delivery materials, such as polyethylene oxide/polypropylene oxide block copolymers (e.g. poloxamers), poly-orthoesters, cross-linked polyvinyl alcohol, polyanhydrides, polymethacrylate and polymethacryladmide hydrogels, anionic carbohydrate polymers, etc.. Useful delivery systems are well known in the art and are described in, e.g., U.S. Pat. No. 4,937,254, the entire disclosure of which is hereby incorporated by reference.

One particularly suitable formulation to achieve the desired near pseudo zero-order release of manoalide comprise injectable microcapsules or microspheres prepared from a biodegradable polymer, such as poly(dl-lactide), poly(dl-lactide-co-glycolide), poly-caprolactone, polyglycolide, polylactic acid-co-glycolide, poly (hydroxybutyric acid), a polyortho-ester or a polyacetal.

Injectable systems comprising microcapsules or microspheres of a diameter on the order of about 50 to about 500 µm offer advantages over other delivery systems. For example, they generally use less active agent and may be administered by paramedical personnel. Moreover, such systems are inherently flexible in the design of the duration and rate of separate drug release by selection of microcapsule size, drug loading and dosage administered. In addition, such microcapsules can be successfully sterilized with gamma irradiation.

Microcapsules are systems comprising a polymeric wall that encloses a liquid or solid core. The capsule wall usually does not react with the core material; however, it is designed to provide sufficient strength to enable normal handling without rupture while being sufficiently thin to allow a high core to wall volume ratio. The capsule contents remain within the wall until released by diffusion or other means that dissolve, melt, break, rupture or remove the capsule material. Preferably, the capsule wall can be made to degrade and decompose in suitable environments while diffusing the core material through the capsule wall to allow for its slow, prolonged delivery.

The mechanism of release in biodegradable microcapsules is a combination of drug diffusion and polymer biodegradation. Therefore, the rate and duration of release are determined by microcapsule size, drug content and quality, and polymer parameters such as crystallinity, molecular weight and composition. In particular, adjustment in the amount of drug released is generally achieved by modification of capsule wall thickness, capsule diameter, or both. Detailed information concerning the design, preparation and use of microspheres and microcapsules is provided by, e.g., Lewis, D. H., "Controlled Release of Bioactive Agents from Lactide/Glycolide Polymers," in "Biodegradable Polymers as Drug Delivery Systems," Jason & Langer, eds., pp. 1–41 (1990), the entire disclosure of which is hereby incorporated by reference. The sustained intraperitoneal release of dexamethasone using poly(lactide-co-glycolide) microparticles is described in Hoeckel, M. et al., "Prevention of Peritoneal Adhesions in the Rat with Sustained Intraperitoneal Dexamethasone Delivered by a Novel Therapeutic System," *Annales Chirurgiae et Gynaecologiae*, Vol. 76, pp. 306–313 (1987), the entire disclosure of which is also incorporated by reference.

As is well known to those skilled in the art, various methods are currently available for preparing microcapsules, any of which could be employed to provide formulations in accordance with the present invention. Biodegradable polymeric materials suitable for preparation of microcapsules for controlled (i.e., near zero-order) release would be readily determined through routine experimentation by those skilled in the art. Moreover, alternative delivery systems suitable for use in accordance with the present invention (for example, fibers or filaments comprising the active agents) based on biodegradable polymers are also contemplated as within the scope of the present invention.

An alternative approach for the single-dose delivery of manoalide involves the use of biodegradable polymers, such as the ones described above, in the form of a film. Such films may be produced by spraying or discharging dispersed liquid droplets containing the biopolymer and manoalide in a suitable carrier from a pressurized container onto the targeted site.

Another approach for the single-dose delivery of manoalide, in accordance with the present invention, involves the use of liposomes and other lipid-based delivery systems. The encapsulation of an active agent in multilamellar vesicles (or liposomes) is a well known technique used to assist in target drug delivery and prolong drug residence. In a typical procedure, a liposome-forming powdered lipid mixture is added to the desired quantity of active agent in aqueous solution (e.g., phosphate buffered saline) to form a suspension. After a suitable hydration period, the hydrated suspension is then autoclaved to provide the liposome-active agent preparations. A lipid mixture suitable for formation of liposomes may be prepared from L-alpha-distearoyl phosphatidylcholine and cholesterol dissolved in chloroform, to which alpha-tocopherol is added; other compositions and methods for formation of liposomes would, however, also be useful for this purpose. The intraperitoneal administration of liposomes containing ibuprofen or tolmetin is described in Rodgers, K. et al., "Inhibition of Postsurgical Adhesions by Liposomes Containing Nonsteroidal Anti-inflammatory Drugs," *Int. J. Fertil.*, Vol. 35, p. 40 (1990), the entire disclosure of which is hereby incorporated by reference.

Other lipid-based delivery systems are also contemplated for use in this invention. One useful system includes lipid foams such as DepoFoam extended-release formulations comprising spherical particles bounded by a single bilayer lipid membrane and each containing numerous nonconcentric aqueous chambers which encapsulate the active ingredient (see, e.g, Kim, T. K. et al. (1993) "Extended-release formulation of morphine for subcutaneous administration," *Cancer Chemother. Pharmacol.*, Vol. 33, 187; Chatelut, E. et al. (1993) "A slow-release methotrexate formulation for intrathecal chemotherapy," *Cancer Chemother. Pharmacol.*, Vol. 32, 179.] Such lipid particles are made from nontoxic lipids identical to those found in cell membranes.

Another suitable lipid-based delivery system for delivering manoalide according to the invention includes emulsion carrier systems based on egg sphinomyelin and egg phosphatidylcholine. Such emulsion carrier systems have prolonged blood circulation retention times and were developed for delivering highly lipophilic drugs. T. Takino et al. (1994) "Long Circulating Emulsion Carrier Systems for Highly Lipophilic Drugs," *Biol. Pharm. Bull.*, Vol. 17, pp. 121–125.

Yet another suitable approach for single dose delivery of manoalide in accordance with the present invention involves the use of so-called crystalloid and viscous instillares. Crystalloids are known in the art as water soluble crystalline substances, e.g., NaCl, capable of diffusing through a semipermeable membrane. Solutions of crystalloids, such as saline, are known as crystalloids, crystalloid solutions or crystalloid instillates. Crystalloid instillates include, but are not limited to, lactated Ringer's solution, saline and phosphate buffered saline. In the case of viscous instillares, high-molecular-weight carriers used in admixture with the active agents include, but are not limited to, the following: dextrans and cyclodextrans; hydrogels; cross-linked viscous materials, including viscoelastics and cross-linked viscoelastics; carboxymethylcellulose; hyaluronic acid; cross-linked hyaluronic acid, and hyaluronic acid compounded with orthoesters. While some studies have suggested that the use of viscous barrier solutions per se may have an advantageous effect in reducing the incidence of adhesion formation, it is believed that any such effect is of limited scope when compared to the combination of manoalide and carrier. The intraperitoneal administration of a viscous instillate comprising tolmetin is described in Abe, H. et al., "The Effect of intra-peritoneal Administration of Sodium Tolmetin-Hyaluronic Acid on the Postsurgical Cell Infiltration In Vivo," *J Surg. Res.*, Vol. 49, p. 322 (1990), the entire disclosure of which is hereby incorporated by reference.

Pursuant to yet another approach, manoalide is administered in combination with an absorbable mechanical barrier which alone reduces adhesion formation. As would be readily apparent to one working in the field, manoalide may be covalently or non-covalently (e.g., ionically) bound to such a barrier, or it may simply be dispersed therein. A particularly suitable mechanical barrier for use in this particular embodiment of the invention comprises hydroxyethyl starch which is described in U.S. patent application Ser. No. 08/482,235, filed concurrently with this application, entitled HYDROXYETHYL STARCH AND USE THEREOF AS ANABSORBABLE MECHANICAL BARRIER AND INTRACAVITY CARRIER DEVICE by Gere diZerega (University of Southern California, assignee), and incorporated by reference in its entirety.

Another suitable mechanical barrier for use in this invention includes oxidized regenerated cellulose which is available under the designation INTERCEED(TC7) from Johnson and Johnson Medical, Inc., New Brunswick, N.J. [INTERCEED(TC7) Adhesion Barrier Study Group, "Prevention of postsurgical adhesions by INTERCEED(TC7), an absorbable adhesion barrier: a prospective, randomized multicenter clinical study," *Fertility and Sterility*, Vol. 51, p. 933 (1989)]. The use of a mechanical barrier as a carrier to deliver heparin to traumatized surfaces is disclosed in Diamond, M. P. et al., "Synergistic effects of INTERCEED (TC7) and heparin in reducing adhesion formation in the rabbit uterine horn model," *Fertility and Sterility*, Vol. 55, p. 389 (1991) and Diamond, M. P. et al., "Adhesion reformation: reduction by the use of INTERCEED(TC7) plus heparin," *J. Gyn. Surg.*, Vol. 7, p. 1 (1991), the entire disclosures of which are hereby incorporated by reference.

The invention may be better understood with reference to the accompanying examples, which are intended to be illustrative only and should not be viewed as in any sense limiting the scope of the invention, which is defined hereinafter in the accompanying claims.

EXAMPLES

Multiple studies to confirm the efficacy of manoalide in the reduction of adhesion formation after peritoneal surgery were performed. Two model systems were employed: the sidewall adhesion model and the uterine horn model. A clear correlation between results obtained using both of these models and utility in adhesion prevention has been demonstrated with INTERCEED(TC7), for which clear clinical efficacy has been shown and FDA approval for adhesion prevention in gynecological surgery has been obtained.

In the peritoneal sidewall model, rabbits were pre-anesthetized with 1.2 mg/kg acetylpromazine and anesthetized with a mixture of 55 mg/kg ketamine hydrochloride and 5 mg/kg xylazine intramuscularly. Following preparation for sterile surgery, a midline laparotomy was performed. A 3×5-cm area of peritoneum and transversus abdominis muscle was removed on the right lateral abdominal wall. The cecum was exteriorized, and digital pressure was exerted to create subserosal hemorrhages over all cecal surfaces. The cecum was then returned to its normal anatomic position. The compound to be tested was placed in an Alzet miniosmotic pump (Alza Corporation, Palo Alto, Calif., USA) to allow continuous release of the molecule through the postsurgical interval. The Alzet miniosmotic pump was placed in the subcutaneous space and a delivery tube connected the pump with the site of injury at sidewall. Vehicle was placed in the pump of control rabbits. The abdominal wall and skin were closed in a standardized manner.

After 7 days, the rabbits were sacrificed and the percentage of the area of the sidewall injury that is involved in adhesions was determined. In addition, the tenacity of the adhesion formed was scored using a system as follows:

| | |
|---|---|
| 0 = | No adhesions |
| 1 = | mild, easily dissectable adhesions |
| 2 = | moderate adhesions; non-dissectable, does not tear organ |
| 3 = | dense adhesions; non-dissectable, tears when removed |

A reduction in the area or the tenacity of the adhesions would be considered beneficial.

In additional experiments, a rabbit uterine horn model was employed. This model has been previously shown to cause severe adhesions in rabbits after surgery [Nishimura, K. et al., "The Use of Ibuprofen for the Prevention of Postoperative Adhesions in Rabbits," Am. J. Med., Vol. 77, pp. 102–106 (1984)]. The rabbits were anesthetized (130 mg/kg ketamine and 20 mg/kg acetylpromazine im) and prepared for sterile surgery. A midline laparotomy was performed, and surgical trauma was performed on both uterine horns by abrading the serosal surface with gauze until punctate bleeding developed. Ischemia of both uterine horns was induced by removal of the collateral blood supply. After traumatization, the abdominal wall was closed in two layers. The compound to be tested was delivered as described for the peritoneal sidewall model, but the tubing was placed over the injured uterine horns.

With the uterine horn model, an initial score to represent the overall extent of adhesions is given (0 to 4+). The percentage of a surface of the horn involved in adhesions to various organs are given in the tables below the overall adhesion score.

In the model systems employed in the examples, manoalide was shown to reduce the incidence of peritoneal adhesions. In these Examples, the drug was delivered to the targeted site at a rate of 10 µl/hour. The two dosage concentrations employed were 0.1 and 1 µg/ml. For purposes of preventing adhesion formation in accordance with the present invention, it is not believed that high systemic levels of manoalide would be necessary.

EXAMPLE 1

Assay for Measuring Inhibition of PLA Activity

In this Example, a assay procedure is provided to identify manoalide derivatives or analogs which inhibit PLA activity. The ability of manoalide or a manoalide analogue to inhibit phospholipase A2 may be measured by the method disclosed by Glaser and Jacobs (1987), Biochemical Pharmacology, Vol. 36, pp. 2079–2086.

According to the Glaser procedure, bee venom $PLA_2$ (mol wt 15,800) activity is determined using a substrate solution containing mixed micelles of 1.36 mM dipalmitoyl phosphatidylcholine, 2.76 mM Triton X-100, 0.5 µCi of labeled dipalmitoyl phosphatidylcholine prepared in 10 mM 4-(2-hydropyethyl)-1-piperazine-ethanesulfonic acid (HEPES), 1 mM $CaCl_2$, pH 7.4 at 41° C. Approximately 25 nM enzyme (0.2 µg protein) is added to 500 µl of the substrate solution, and the mixture is incubated at 41° C for 15 sec. Released $^3H$-palmitic acid extracted and quantitated for the purposes of calculating $PLA_2$ activity. The ability of a manoalide analogue to inhibit bee venom $PLA_2$ activity will be determined after preincubation of the test compound at a concentration ranging from 1 pg to 10 mg per ml of the enzyme solution for 1 hr at 41° C. prior to measurement of activity.

EXAMPLE 2

Sidewall Model Evaluation of Manoalide

The efficacy of manoalide (available from Calbiochem at La Jolla, Calif., USA) in preventing adhesion formation was evaluated at two dosage concentrations in a sidewall model. The drug was placed in a Alzet miniosmotic pump and delivered over 7 days at a rate of 10 µl/hr and the animals were sacrificed after 7 days. The vehicle used was 10% ethanol in saline. Relative to the control, manoalide administration reduced the area of adhesion formation in this sidewall model. No inflammation or precipitation noted at the site of injury. The results are summarized in Table 1. A student t test analysis of the data was performed and the results are also reported in Table 1.

TABLE 1

| Treatment | % Adhesions | Adhesion Score |
|---|---|---|
| Vehicle Control | 90% | 2+ |
| | 90% | 1+ |
| | 80% | 2+ |
| | 70% | 2+ |
| | 60% | 2+ |
| | 80% | 2+ |
| Mean: | 78.3% ± 10.7 | |
| 1.0 µg/ml Manoalide | 20% | 2+ |
| | 20% | 1+ |
| | 0% | 0+ |
| | 30% | 2+ |
| | 5% | 1+ |
| | 20% | 1+ |
| Mean[a]: | 15.8% ± 10.17 | |
| 0.1 µg/ml Manoalide | 10% | 2+ |
| | 60% | 1+ |
| | 5% | 2+ |

TABLE 1-continued

| Treatment | % Adhesions | Adhesion Score |
|---|---|---|
|  | 5% | 1+ |
|  | 50% | 2+ |
|  | 30% | 1+ |
| Mean[a]: | 26.7% ± 21.92 |  |

[a] $p = 0.000$

EXAMPLE 3

DUH Model Evaluation of Manoalide

The efficacy of manoalide in preventing adhesion formation was evaluated at two doses in a double uterine horn (DUH) model. The drug was delivered via an Alzet miniosmotic pump for 7 days at a rate of 10 μl/hr and the animals were sacrificed after 7 days. The vehicle used was 10% ethanol in saline. Statistical analysis was performed on the overall score of the nonparametric double uterine horn model data. The data was rank ordered, a rank value was given and an analysis of variance on the ranks was performed. The results are summarized in Tables 2 and 3. Relative to the control, manoalide was efficacious in reducing adhesion formation in this model.

TABLE 2

| TREATMENT | ADHESION SCORE |
|---|---|
| Vehicle Control | 3+ |
|  | 3+ |
|  | 3.5+ |
|  | 3+ |
|  | 3.5+ |
|  | 3.5+ |
| 1.0 μg/ml Manoalide | 1.5+ |
|  | 1+ |
|  | 1.5+ |
|  | 1.5+ |
|  | 1.5+ |
|  | 1+ |
| 0.1 μg/ml Manoalide | 2+ |
|  | 1+ |
|  | 1+ |
|  | 1+ |
|  | 1+ |
|  | 1.5+ |
|  | 2+ |

TABLE 3

| | % Organ Involvement in Uterine Horn Adhesion | | | | | | | |
|---|---|---|---|---|---|---|---|---|
| | Right Horn | | | | Left Horn | | | |
| Treatment | Bowel | Bladder | Itself | Left | Bowel | Bladder | Itself | Right |
| Control | 40 | 20 | 60 | 40 | 40 | 20 | 60 | 40 |
|  | 0 | 60 | 40 | 60 | 0 | 60 | 50 | 60** |
|  | 30 | 60 | 60 | 40 | 30 | 60 | 40 | 40** |
|  | 30 | 40 | 40 | 20 | 30 | 40 | 40 | 20** |
|  | 40 | 60 | 60 | 50 | 40 | 60 | 40 | 50** |
|  | 50 | 60 | 50 | 80 | 50 | 60 | 50 | 80** |
| Mean | 31.7 | 50 | 51.7 | 48.3 | 31.7 | 50 | 46.7 | 48.3 |
| 1.0 μg/ml Manoalide | 10 | 0 | 20 | 10 | 10 | 0 | 10 | 10 |
|  | 10 | 0 | 10 | 0 | 10 | 0 | 20 | 0 |
|  | 0 | 10 | 60 | 0 | 0 | 10 | 30 | 0* |
|  | 30 | 0 | 20 | 0 | 30 | 10 | 10 | 0* |
|  | 0 | 30 | 20 | 0 | 0 | 30 | 0 | 0 |
|  | 0 | 0 | 10 | 10 | 0 | 0 | 10 | 10 |
| Mean | 8.3 | 6.7 | 23.3 | 3.3 | 8.3 | 8.3 | 13.3 | 3.3 |
| 0.1 μg/ml Manoalide | 10 | 0 | 20 | 10 | 10 | 0 | 20 | 10 |
|  | 0 | 0 | 10 | 20 | 0 | 0 | 0 | 20 |
|  | 10 | 0 | 30 | 0 | 10 | 0 | 10 | 0 |
|  | 0 | 10 | 20 | 10 | 0 | 10 | 10 | 10 |
|  | 0 | 10 | 10 | 0 | 0 | 20 | 20 | 0 |
|  | 10 | 0 | 20 | 20 | 10 | 0 | 10 | 20* |
| Mean | 5 | 3.3 | 18.3 | 10 | 5 | 5 | 11.7 | 10 |

*Bladder, horn or bowel adhered to the sidewall (at either tube or tube suture)
**Horn and bowel or bladder to sidewall Statistical analysis was performed on the overall score of the nonparametric data taken from Table 2. The data was rank ordered and assigned a rank value. Analysis of the variance of the ranks was then performed and the resulting student t test results are summarized below.

| Group | Rank ± Std. Dev. | p Value |
|---|---|---|
| Control | 15.5 ± 1.5 | — |
| 1 μg/ml Manoalide | 6.3 ± 2.36 | 0.000 |
| 0.1 μg/ml Manoalide | 6.7 ± 3.85 | 0.000 |

EXAMPLE 4

Kinetic DUH Model Evaluation of Mannolide

The efficacy of manoalide in the rabbit double uterine horn model was further evaluated in a kinetics study. In this study, the pump was disconnected (D/C) at various times after surgery (24, 48, or 72 hours) to determine the time period of exposure to the drug effective to reduce adhesion formation. The results are summarized in Tables 4 and 5.

TABLE 4

| TREATMENT | ADHESION SCORE |
|---|---|
| Vehicle Control | 3+ |
| | 3.5+ |
| | 2.5+ |
| | 3+ |
| | 3.5+ |
| | 2.5+ |
| 1.0 μg/ml Manoalide 24 hour D/C | 1.5+ |
| | 1+ |
| | 1+ |
| | 1.5+ |
| | 1+ |
| | 1.5+ |
| 1.0 μg/ml Manoalide 48 hr D/C | 0.5+ |
| | 1.5+ |
| | Infection |
| | 2+ |
| | 1+ |
| | 1.5+ |
| 1.0 μg/ml Manoalide 72 hour D/C | 1+ |
| | 1+ |
| | 1.5+ |
| | 0.5+ |
| | 1.5+ |
| | 1.5+ |

TABLE 4-continued

| TREATMENT | ADHESION SCORE |
|---|---|
| 0.1 μg/ml Manoalide 24 hour D/C | 1.5+ |
| | 1.5+ |
| | 2+ |
| | 2+ |
| | 1+ |
| | 1.5+ |
| 0.1 μg/ml Manoalide 48 hour D/C | 1+ |
| | 2+ |
| | 1.5+ |
| | 1+ |
| | 2+ |
| | 1.5+ |
| 0.1 μg/ml Manoalide 72 hour D/C | 2+ |
| | 1.5+ |
| | 1+ |
| | 1.5+ |
| | 1.5+ |
| | 1.5+ |

TABLE 5

| | % Organ Involvement in Uterine Horn Adhesion | | | | | | | |
|---|---|---|---|---|---|---|---|---|
| | Right Horn | | | | Left Horn | | | |
| Treatment | Bowel | Bladder | Itself | Left | Bowel | Bladder | Itself | Right |
| Control | 40 | 20 | 40 | 50 | 40 | 20 | 40 | 50** |
| | 100 | 40 | 50 | 0 | 100 | 40 | 20 | 0** |
| | 40 | 40 | 10 | 0 | 40 | 40 | 40 | 0** |
| | 20 | 50 | 40 | 40 | 20 | 50 | 30 | 40** |
| | 60 | 40 | 50 | 40 | 60 | 40 | 30 | 40** |
| | 50 | 50 | 40 | 0 | 50 | 50 | 20 | 0** |
| Mean | 51.7 | 40 | 38.3 | 21.7 | 51.7 | 40 | 30 | 21.7 |
| 1.0 μg/ml Manoalide 24 D/C | 20 | 0 | 20 | 20 | 20 | 0 | 20 | 20 |
| | 0 | 0 | 10 | 10 | 0 | 0 | 10 | 10 |
| | 0 | 0 | 10 | 10 | 0 | 0 | 0 | 10* |
| | 0 | 0 | 10 | 10 | 0 | 0 | 10 | 10** |
| | 10 | 0 | 10 | 0 | 10 | 0 | 10 | 0* |
| | 0 | 20 | 20 | 0 | 0 | 0 | 10 | 0 |
| Mean | 5 | 3.3 | 13.3 | 8.3 | 5 | 0 | 10 | 8.3 |
| 1.0 μg/ml Manoalide 48 D/C | 0 | 0 | 10 | 0 | 0 | 0 | 20 | 0 |
| | 10 | 0 | 20 | 10 | 10 INFECTION | 0 | 20 | 10 |

TABLE 5-continued

| | % Organ Involvement in Uterine Horn Adhesion | | | | | | | |
|---|---|---|---|---|---|---|---|---|
| | Right Horn | | | | Left Horn | | | |
| Treatment | Bowel | Bladder | Itself | Left | Bowel | Bladder | Itself | Right |
| | 30 | 20 | 0 | 0 | 30 | 20 | 10 | 0** |
| | 30 | 0 | 0 | 0 | 0 | 0 | 20 | 0 |
| | 0 | 20 | 10 | 0 | 0 | 20 | 10 | 0* |
| Mean | 14 | 8 | 8 | 2 | 8 | 8 | 16 | 2 |
| 1.0 µg/ml Manoalide 72 D/C | 0 | 0 | 20 | 10 | 0 | 0 | 10 | 10* |
| | 20 | 0 | 10 | 0 | 20 | 0 | 0 | 0 |
| | 10 | 20 | 0 | 0 | 0 | 20 | 10 | 0 |
| | 0 | 0 | 20 | 0 | 0 | 0 | 10 | 0 |
| | 10 | 0 | 20 | 20 | 10 | 0 | 20 | 20 |
| | 0 | 0 | 20 | 10 | 0 | 0 | 20 | 10 |
| Mean | 6.7 | 3.3 | 15 | 6.7 | 5 | 3.3 | 11.7 | 6.7 |
| 0.1 µg/ml Manoalide 24 D/C | 0 | 10 | 30 | 10 | 0 | 0 | 20 | 10 |
| | 0 | 10 | 0 | 0 | 0 | 10 | 30 | 0* |
| | 10 | 10 | 10 | 10 | 10 | 10 | 10 | 10 |
| | 30 | 10 | 20 | 0 | 30 | 10 | 10 | 0* |
| | 10 | 0 | 10 | 0 | 10 | 0 | 10 | 0 |
| | 0 | 0 | 20 | 30 | 0 | 0 | 20 | 30 |
| Mean | 8.3 | 6.7 | 15 | 8.3 | 8.3 | 5 | 18.3 | 11.7 |
| 0.1 µg/ml Manoalide 48 D/C | 0 | 10 | 10 | 0 | 0 | 10 | 10 | 0 |
| | 20 | 10 | 10 | 10 | 20 | 10 | 10 | 10* |
| | 0 | 10 | 20 | 0 | 0 | 10 | 10 | 0* |
| | 0 | 20 | 0 | 0 | 0 | 20 | 20 | 0* |
| | 0 | 0 | 20 | 10 | 0 | 0 | 20 | 10* |
| | 20 | 0 | 20 | 10 | 20 | 0 | 20 | 10* |
| Mean | 6.7 | 8.3 | 13.3 | 5 | 6.7 | 8.3 | 15 | 5 |
| 0.1 µg/ml Manoalide 72 D/C | 30 | 30 | 20 | 0 | 30 | 30 | 20 | 0 |
| | 20 | 0 | 0 | 0 | 20 | 0 | 10 | 0 |
| | 10 | 0 | 10 | 0 | 10 | 0 | 10 | 0 |
| | 10 | 0 | 10 | 10 | 10 | 0 | 10 | 10 |
| | 10 | 0 | 20 | 20 | 0 | 0 | 20 | 20 |
| | 10 | 10 | 10 | 0 | 10 | 10 | 10 | 0 |
| Mean | 15 | 6.7 | 11.7 | 5 | 11.7 | 6.7 | 13.3 | 5 |

*Bladder, horn or bowel adhered to the sidewall (at either tube or tube suture)
**Horn and bowel or bladder to sidewall Statistical analysis was performed on the overall score of the nonparametric data taken from Table 4. The data was rank ordered and assigned a rank value. Analysis of the variance of the ranks was then performed and the resulting student t test results are summarized below.

| Group | Rank ± Std. Dev. | p Value |
|---|---|---|
| Control | 38.5 ± 1.6 | |
| 1 µg//ml Manoalide 24 hr | 14.3 ± 6.8 | 0.000 |
| 1 µg/ml Manoalide 48 hr | 16.7 ± 11.0 | 0.000 |
| 1 µg/ml Manoalide 72 hr | 13.3 ± 8.0 | 0.000 |
| 0.1 µg/ml Manoalide 24 hr | 22.6 ± 8.5 | 0.001 |
| 0.1 µg/ml Manoalide 48 hr | 20.3 ± 10.22 | 0.002 |
| 0.1 µg/ml Manoalide 72 hr | 20.7 ± 7.3 | 0.000 |

While the fundamental novel features of the invention has been shown and described, it will be understood that various omissions, substitutions and changes in the form and details illustrated may be made by those skilled in the art without departing from the spirit of the invention. It is the intention, therefore, to be limited only as indicated by the scope of the following claims.

What is claimed is:

1. A method for reducing post-surgical adhesion formation between tissue surfaces in a body cavity comprising administering an effective therapeutic amount of manoalide for a period of time sufficient to permit tissue repair.

2. The method according to claim 1, wherein said tissue repair comprises re-epithelization.

3. The method according to claim 1, wherein said tissue repair comprises mesothelial repair.

4. The method according to claim 1, wherein said manoalide is administered in conjunction with a delivery vehicle.

5. The method according to claim 4, wherein said delivery vehicle is in the form of microcapsules or microspheres.

6. The method according to claim 5, wherein the microcapsules or microspheres comprise a biodegradable polymer selected from the group consisting of poly(dl-lactides), poly(dl-lactide-co-glycolides), polycaprolactones, polyglycolides, polylactic acid-co-glycolides, poly (hydroxybutyric acids), polyortho-esters, polyacetals and mixtures thereof.

7. The method according to claim 4, wherein said delivery vehicle is in the form of a film.

8. The method according to claim 7, wherein the film comprises a biodegradable polymer selected from the group consisting of poly(dl-lactides), poly(dl-lactide-co-glycolides), polycaprolactones, polyglycolides, polylactic acid-co-glycolides, poly(hydroxybutyric acids), polyortho-esters, polyacetals and mixtures thereof.

9. The method according to claim 4, wherein said delivery vehicle is in the form of a liposome.

10. The method according to claim 9, wherein the liposome comprises L-alpha-distearoyl phosphatidylcholine.

11. The method according to claim 4, wherein said delivery vehicle is in the form of a lipid foam.

12. The method according to claim 4, wherein said delivery vehicle is in the form of an instillate.

13. The method according to claim 12, wherein the instillate comprises a crystalloid carrier selected from the group consisting of phosphate buffered saline, saline, and lactated Ringer's solution.

14. The method according to claim 12, wherein the instillate comprises a high-molecular-weight carrier selected from the group consisting of dextrans, cyclodextrans, hydrogels, carboxymethylcellulose, hyaluronic acid, crosslinked hyaluronic acid, hyaluronic acid compounded with orthoesters, chondroitin sulfate and mixtures thereof.

15. The method according to claim 1, wherein the manoalide is administered in combination with an absorbable mechanical barrier.

16. The method according to claim 15, wherein the absorbable mechanical barrier comprises hydroxyethyl starch.

17. The method according to claim 15, wherein the absorbable mechanical barrier comprises oxidized regenerated cellulose.

18. The method according to claim 1, wherein said manoalide is administered at a dosage ranging between about 0.0004 ng/hr/kg and about 0.4 mg/hr/kg.

19. The method according to claim 18, wherein said manoalide is administered at a dosage ranging between about 0.04 ng/hr/kg and about 0.004 mg/hr/kg.

20. The method according to claim 1, wherein said manoalide is administered at a dosage ranging between about 0.000067 ng/hr/cm$^2$ and about 0.067 mg/hr/cm$^2$.

21. The method according to claim 20, wherein said manoalide is administered at a dosage ranging between about 0.0067 ng/hr/cm$^2$ and 0.67 µg/hr/cm$^2$.

* * * * *